US008207238B2

(12) United States Patent
Holmes et al.

(10) Patent No.: US 8,207,238 B2
(45) Date of Patent: Jun. 26, 2012

(54) DENTAL COMPOSITIONS AND INITIATOR SYSTEMS WITH COLOR-STABLE AMINE ELECTRON DONORS

(75) Inventors: Brian N. Holmes, St. Paul, MN (US); Gregory A. Kobussen, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 41 days.

(21) Appl. No.: 12/740,466

(22) PCT Filed: Oct. 29, 2008

(86) PCT No.: PCT/US2008/081559
§ 371 (c)(1),
(2), (4) Date: Apr. 29, 2010

(87) PCT Pub. No.: WO2009/058843
PCT Pub. Date: May 7, 2009

(65) Prior Publication Data
US 2010/0311858 A1 Dec. 9, 2010

Related U.S. Application Data

(60) Provisional application No. 60/984,470, filed on Nov. 1, 2007.

(51) Int. Cl.
*C08F 2/50* (2006.01)
(52) U.S. Cl. ............... 522/25; 522/15; 522/31
(58) Field of Classification Search ............. 522/15–908
See application file for complete search history.

(56) References Cited

U.S. PATENT DOCUMENTS

| | | | |
|---|---|---|---|
| 4,071,424 A * | 1/1978 | Dart et al. ........ | 522/14 |
| 4,259,075 A | 3/1981 | Yamauchi | |
| 4,356,296 A | 10/1982 | Griffith | |
| 4,439,380 A * | 3/1984 | Michl et al. ........ | 264/16 |
| 4,499,251 A | 2/1985 | Omura | |
| 4,503,169 A | 3/1985 | Randklev | |
| 4,507,382 A * | 3/1985 | Rousseau et al. ......... | 430/275.1 |
| 4,507,497 A * | 3/1985 | Reilly, Jr. ........ | 562/441 |
| 4,511,646 A * | 4/1985 | Fohrenkamm et al. .... | 430/283.1 |
| 4,536,523 A * | 8/1985 | Antonucci .......... | 523/115 |
| 4,537,940 A | 8/1985 | Omura | |
| 4,539,382 A | 9/1985 | Omura | |
| 4,553,941 A * | 11/1985 | Aasen ........... | 433/228.1 |
| 4,593,054 A * | 6/1986 | Asmussen et al. .......... | 523/118 |
| 4,629,746 A | 12/1986 | Michl | |
| 4,642,126 A | 2/1987 | Zador | |
| 4,648,843 A | 3/1987 | Mitra | |
| 4,652,274 A | 3/1987 | Boettcher | |
| 4,665,217 A | 5/1987 | Reiners | |
| 4,695,251 A | 9/1987 | Randklev | |
| 4,752,338 A | 6/1988 | Reiners | |
| 4,767,798 A | 8/1988 | Gasser | |
| 4,872,936 A | 10/1989 | Engelbrecht | |
| 4,882,365 A | 11/1989 | Gasser | |
| 5,026,902 A | 6/1991 | Fock | |
| 5,037,579 A * | 8/1991 | Matchett ........... | 516/90 |
| 5,076,844 A | 12/1991 | Fock | |
| 5,130,347 A | 7/1992 | Mitra | |
| 5,154,762 A | 10/1992 | Mitra | |
| 5,426,134 A | 6/1995 | Rheinberger | |
| 5,501,727 A * | 3/1996 | Wang et al. .......... | 106/35 |
| 5,530,038 A | 6/1996 | Yamamoto | |
| 5,545,676 A * | 8/1996 | Palazzotto et al. .......... | 522/15 |
| 5,998,495 A * | 12/1999 | Oxman et al. .......... | 522/15 |
| 6,025,406 A * | 2/2000 | Oxman et al. .......... | 522/14 |
| 6,030,606 A | 2/2000 | Holmes | |
| 6,043,295 A * | 3/2000 | Oxman et al. .......... | 522/14 |
| 6,306,926 B1 | 10/2001 | Bretscher | |
| 6,387,981 B1 * | 5/2002 | Zhang et al. .......... | 523/117 |
| 6,458,868 B1 | 10/2002 | Okada | |
| 6,566,413 B1 | 5/2003 | Weinmann | |
| 6,572,693 B1 | 6/2003 | Wu | |
| 6,624,236 B1 | 9/2003 | Bissinger | |
| 6,730,156 B1 * | 5/2004 | Windisch et al. .......... | 106/35 |
| 6,852,795 B2 | 2/2005 | Bissinger | |
| 6,852,822 B1 | 2/2005 | Bissinger | |
| 6,899,948 B2 | 5/2005 | Zhang | |
| 2002/0156152 A1 * | 10/2002 | Zhang et al. .......... | 523/115 |
| 2003/0166740 A1 | 9/2003 | Mitra | |
| 2003/0195273 A1 | 10/2003 | Mitra | |
| 2005/0252413 A1 | 11/2005 | Kangas | |
| 2005/0252414 A1 | 11/2005 | Craig | |
| 2005/0256223 A1 | 11/2005 | Kolb | |

FOREIGN PATENT DOCUMENTS

| | | |
|---|---|---|
| EP | 0189540 A2 | 8/1986 |
| EP | 0201031 | 11/1986 |
| EP | 0201778 | 11/1986 |
| EP | 0373384 | 6/1990 |
| EP | 238025 | 12/1992 |
| EP | 712622 | 9/1999 |
| EP | 1051961 | 11/2000 |
| WO | WO 9700065 A1 * | 1/1997 |
| WO | WO 9847046 A1 * | 10/1998 |
| WO | WO 9847047 A1 * | 10/1998 |
| WO | WO 00/38619 | 7/2000 |
| WO | WO 00/42092 | 7/2000 |
| WO | WO 01/07444 | 2/2001 |
| WO | WO 01/92271 | 12/2001 |
| WO | WO 03/063804 | 8/2003 |
| WO | WO 2004/060327 | 7/2004 |
| WO | WO 2006/020760 | 2/2006 |
| WO | WO 2007/079070 | 7/2007 |

OTHER PUBLICATIONS

Adamson et al.; JCSOA9; J. Chem. Soc.; (1949); spl., pp. 144, 152.

(Continued)

*Primary Examiner* — James J Seidleck
*Assistant Examiner* — Peter A Salamon
(74) *Attorney, Agent, or Firm* — Julie A. Lepos-Kuchar

(57) ABSTRACT

The invention features a hardenable dental composition, e.g., polymerizable dental restoratives, adhesives, etc., that contain a color-stable amine electron donor in an initiation system for initiating polymerization of the composition.

27 Claims, No Drawings

OTHER PUBLICATIONS

ANSI/ADA Specification No. 27, "Resin-Based Filling Materials", (1993), pp. 1-36.
Boberg, JLACBF; Justus Liebigs Ann. Chem.; Bd 683; 1965; pp. 132-148.
Elderfield et al., "Experiments on the Synthesis of 4-Hydroxy- and 4-Chloroquinolines from β-Anilinopropionic Acids", Contribution from the Department of Chemistry of Columbia University, Jul. 1946, vol. 68, pp. 1259-1263.
Farahani et al., "A GC-MS study of the addition reaction of aryl amines with acrylic monomers", *Journal of Applied Polymer Sciences*, vol. 67, No. 9, (1998), John Wiley & Sons, Inc., pp. 1545-1551 [XP002585589].
Katritzky et al., "The Preparation of Functionalized Amines and Amides Using Benzotriazole Derivatives and Organozine Reagents", TETRAB; *Tetrahedron*; EN; 54; 25; 1998; pp. 7167-7178.
International Search Report for PCT/US2008/081559, 4 pages.
Written Opinion of the International Search Authority for PCT/US2008/081559, 6 pages.
Yamamiya, "Photocurable coating material", *Chemical Abstracts Service*, Columbus, OH, US, Mar. 19, 1997, [XP002585590] Database Caplus [Online] retrieved from stn Database accession No. 1979:441039.

\* cited by examiner

DENTAL COMPOSITIONS AND INITIATOR SYSTEMS WITH COLOR-STABLE AMINE ELECTRON DONORS

CROSS REFERENCE TO RELATED APPLICATIONS

This application is a national stage filing under 35 U.S.C. 371 of PCT/US2008/081559, filed Oct. 29, 2008, which claims priority to U.S. Application No. 60/984,470, filed Nov. 1, 2007, the disclosure of which is incorporated by reference in its/their entirety herein.

TECHNICAL FIELD

This invention relates to initiator systems for curing polymerizable monomers. More specifically, this invention relates to polymerizable dental compositions that contain a photoinitiator system comprising a color stable amine electron donor that is activated upon exposure to visible light.

BACKGROUND

The restoration of teeth commonly involves the use of (meth)acrylate-based free-radically polymerizable resins that can be chemically cured or light cured. Chemical curing typically involves a redox system with a peroxide oxidizing agent and an amine reducing agent that produces free radicals that initiate polymerization. Light curing typically involves a photoinitiator system that produces free radicals upon exposure to light (400-1000 nm) Photoinitiator systems also have been used in conjunction with cationically cured dental compositions, for example epoxy-based resins, that are cured by way of a cationic ring-opening polymerization curing mechanism. For example, ternary photoinitiator systems comprising an iodonium salt, a visible light absorber (e.g., CPQ), and an electron donor (e.g., a polycyclic aromatic) have been utilized for curing both free-radically cured (meth)acrylate resins and cationically cured epoxy resins.

Many (meth)acrylate-based composite dental restoratives employ ethyl 4-dimethylamino benzoate (EDMAB) as an electron donor in the photo initiator system. Although EDMAB provides good curing properties, dental composite compositions using EDMAB usually require the addition of UV stabilizers, such as benzotriazole derivatives (e.g., TINUVIN P), to achieve adequate color stability. Color stability is an important property for dental restorative compositions since it can impact the long term aesthetics of restorations made from the composition. Many amine electron donors, such as EDMAB, that are used in dental photo initiator systems are susceptible to color formation as a result of photo oxidation processes that occur after curing of the restorative. The addition of a UV stabilizer to the composition helps to prevent this color formation. Unfortunately, UV stabilizers can reduce the fluorescence of the restorative. Since natural teeth fluoresce when irradiated with UV light, restoratives that lack natural tooth fluorescence, for example, because of the presence of a UV stabilizer, will become more noticeable, and thus less aesthetically pleasing, when viewed under UV radiation or "black light" conditions.

SUMMARY

The present invention is directed to polymerizable dental compositions that contain a color-stable amine as an electron donor in the initiator system. In one embodiment, the composition includes (a) a polymerizable component, such as an ethylenically unsaturated compound (e.g., a (meth)acrylate), and (b) an initiator system comprising at least one electron donor having the following formula I:

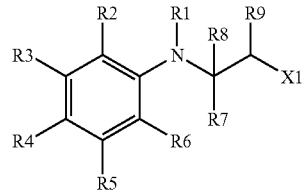

Formula I

In the above formula I, wherein
N is nitrogen;
R1 is an alkyl group having 1 to 16 carbon atoms, or is $CH_2CH_2X2$;
R2, R3, R4, R5, R6, R7, R8, and R9 are independently selected from hydrogen (H) or an alkyl group having 1 to 4 carbon (C) atoms, with the proviso that at least one of the carbon atoms alpha to the nitrogen in the above Formula I is bonded to at least one hydrogen atom.
X1 is selected from $CO_2R10$, $C(O)R11$, $C(O)R10$, and $CONR10R11$ and X2 is selected from CN, $CO_2R10$, $C(O)R11$, and $C(O)R10$, where each R10 and R11 are independently selected from H, alkyl groups having 1 to 6 carbon atoms, aryl groups, and aralkyl groups. Typically X2 is not $CO_2H$. When R1 and/or R4 are —$CH_2$-alkyl, the alkyl component is typically a lower alkyl, i.e. a $C_1$ to $C_4$ alkyl.

The electron donors of Formula I have superior color stability compared to other amine electron donors, such as EDMAB, that are commonly used in dental compositions. They are particularly well-suited for use in, for example, tooth-colored dental restorative compositions where it is generally desirable to avoid unwanted color formation after curing of the composition so that the final restoration retains a natural, tooth-like appearance that matches the color of surrounding teeth for as long as possible. In addition, the use of a color-stable electron donor may reduce or even eliminate the need for a UV stabilizer in the composition. Since UV stabilizers, which are sometimes added to dental compositions to provide color stability, can interfere with the fluorescence of the composition, a reduction in the amount of UV stabilizer allows for better expression of fluorescence, which in turn leads to higher aesthetics.

Suitable electron donors falling within Formula I above include, but are not limited to, the following compounds:

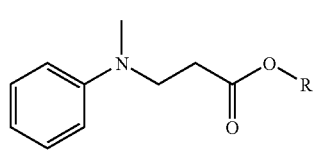

formula 1-a

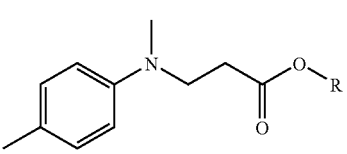

formula 1-b

Where R is an alkyl group having 1 to 4 carbon atoms.

In addition to the color-stable amine, the photoinitiator system may further comprise a visible light sensitizer, for example camphorquinone. Typically, the photopolymerizable composition also comprises an iodonium salt, for example diphenyliodonium hexafluorophosphate. The photoinitiator system may further include one or more additional electron donors. Suitable additional electron donors that may be combined with the color-stable amine include, for example, polycyclic aromatic compounds, such as anthracene derivatives, biphenylene derivatives, or combinations thereof.

The dental composition of the invention may also optionally include a filler system. In some implementations the filler system includes one or more silane-treated nanofillers, selected from nano silica, nano zirconia, zirconia-silica nanoclusters, other metal oxides or particulate glasses and combinations thereof.

The dental compositions of the invention are useful in a variety of dental and orthodontic applications, including as dental restoratives, dental adhesives, dental cements, cavity liners, orthodontic adhesives, dental sealants, dental coatings, and the like. These compositions may be used to prepare dental articles by hardening to form, for example, dental fillings, dental mill blanks, dental crowns, dental prostheses, orthodontic devices, and the like.

The above summary is not intended to describe each embodiment or every implementation of the invention. Other embodiments, features, and advantages of the present invention will be apparent from the following detailed description thereof, and from the claims.

Definitions

The term "electron donor" generally refers to a compound that has a substituent that can donate electrons. Suitable examples include, but are not limited to, a primary amino, secondary amino, tertiary amino, hydroxy, alkoxy, aryloxy, alkyl, or combinations thereof.

By "color-stable" is meant that a disk (1 mm thick by 30 mm in diameter) of cured material has a delta E of 3 units or less as defined and measured using the "Color Test Method" described herein.

As used herein "substantially free of UV stabilizers" means that the the amount of UV stabilizer present in the composition is sufficiently low such that the fluorescence of the composition is not reduced below that of natural tooth fluorescence. In some embodiments of the invention, the amount of UV stabilizer is low enough that it does not result in a visible reduction in the fluorescence of the composition when viewed under UV light. Typically the composition contains less than about 5 wt-%, more typically less than about 1.5 wt-%, and most typically less than about 0.75 wt-% of a UV stabilizer.

By "natural tooth fluorescence" is meant that, when viewed under ultraviolet light, the composition exhibits a fluorescence intensity resembling that of a natural tooth, recognizing that fluorescence of natural teeth varies from subject to subject and the desired closeness of the match of the composition's fluorescence to that of a natural tooth depends on the precise situation and/or aesthetic demands of the patient (e.g., molars and other teeth that are not easily visible may not need to match the natural tooth fluorescence as closely as front teeth).

As used herein, "hardenable" is descriptive of a material or composition that can be cured (e.g., polymerized or crosslinked) or solidified, for example, by removing solvent (e.g., by evaporation and/or heating); heating to induce polymerization and/or crosslinking; irradiating to induce polymerization and/or crosslinking; and/or by mixing one or more components to induce polymerization and/or crosslinking.

By "dental composition" is meant an unfilled or filled (e.g. a composite) material (e.g., a dental or orthodontic material) that are capable of being applied or adhered to an oral surface. Dental compositions include, for example, adhesives (e.g., dental and/or orthodontic adhesives), cements (e.g., glass ionomer cements, resin-modified glass ionomer cements, and/or orthodontic cements), primers (e.g., orthodontic primers), restoratives (e.g., a restorative filling material), liners, sealants (e.g., orthodontic sealants), and coatings. Oftentimes a dental composition can be used to bond a dental article to a tooth structure. By "hardenable dental composition" is meant a dental composition, such as a paste, that can be hardened to form a dental article.

By "dental article" is meant an article that can be adhered (e.g., bonded) to an oral surface (e.g., a tooth structure). Typically, the dental article is a restored dentition or a portion thereof. Examples include restoratives, replacements, inlays, onlays, veneers, full and partial crowns, bridges, implants, implant abutments, copings, anterior fillings, posterior fillings, cavity liners, sealants, dentures, posts, bridge frameworks and other bridge structures, abutments, orthodontic appliances and devices, and prostheses (e.g., partial or full dentures).

As used herein, the terms "dental composition" and "dental article" are not limited to compositions and articles used in dental applications, but also include orthodontic compositions (e.g., orthodontic adhesives) and orthodontic devices (e.g., orthodontic appliances such as retainers, night guards, brackets, buccal tubes, bands, cleats, buttons, lingual retainers, bite openers, positioners, and the like), respectively.

By "oral surface" is meant a soft or hard surface in the oral environment. Hard surfaces typically include tooth structure including, for example, natural and artificial tooth surfaces, bone, tooth models, dentin, enamel, cementum, and the like By "filler" is meant a particulate material suitable for use in the oral environment. Dental fillers generally have an average particle size of at most 100 micrometers.

By "nanofiller" is meant a filler having an average primary particle size of at most 200 nanometers. The nanofiller component may be a single nanofiller or a combination of nanofillers. Typically the nanofiller comprises non-pyrogenic nanoparticles or nanoclusters. By "nanostructured" is meant a material in a form having at least one dimension that is, on average, at most 200 nanometers (e.g., nanosized particles). Thus, nanostructured materials refer to materials including, for example, nanoparticles as defined herein below; aggregates of nanoparticles; materials coated on particles, wherein the coatings have an average thickness of at most 200 nanometers; materials coated on aggregates of particles, wherein the coatings have an average thickness of at most 200 nanometers; materials infiltrated in porous structures having an average pore size of at most 200 nanometers; and combinations thereof. Porous structures include, for example, porous particles, porous aggregates of particles, porous coatings, and combinations thereof.

As used herein "nanoparticles" is synonymous with "nanosized particles," and refers to particles having an average size of at most 200 nanometers. As used herein for a spherical particle, "size" refers to the diameter of the particle. As used herein for a non-spherical particle, "size" refers to the longest dimension of the particle. In certain embodiments, the nanoparticles are comprised of discrete, non-aggregated and non-agglomerate particles.

By "nanocluster" is meant an association of nanoparticles drawn together by relatively weak intermolecular forces that cause them to clump together, i.e. to aggregate. Typically, nanoclusters have an average size of at most 10 micrometers.

As used herein, the term "ethylenically unsaturated compound" is meant to include monomers, oligomers, and polymers having at least one ethylenic unsaturation.

By "polymerization" is meant the forming of a higher weight material from monomers or oligomers. The polymerization reaction also can involve a cross-linking reaction.

By "polycyclic aromatic component" is meant at least one polycyclic organic compound having two or more fused aromatic rings, including their alkyl-, alkoxy-, aryl-, and aryloxy- substituted derivatives. By "fused" is meant two aromatic rings with a shared side or with opposing sides directly joined by carbon-carbon bonds.

As used herein, the term "(meth)acrylate" is a shorthand reference to acrylate, methacrylate, or combinations thereof, and "(meth)acrylic" is a shorthand reference to acrylic, methacrylic, or combinations thereof. As used herein, "(meth) acrylate-functional compounds" are compounds that include, among other things, a (meth)acrylate moiety.

The terms "comprises", "comprising" and variations thereof do not have a limiting meaning where these terms appear in the description and claims.

The recitation herein of numerical ranges by endpoints is intended to include all numbers subsumed within that range (e.g. 1 to 5 includes 1, 1.5, 2, 2.75, 3, 3.80, 4, and 5).

As used herein, "a" or "an" means "at least one" or "one or more" unless otherwise indicated. In addition, the singular forms "a", "an", and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

DETAILED DESCRIPTION

The invention features the use of a class of aromatic amines as electron donors in initiator systems used in polymerizable compositions, such as polymerizable dental compositions, e.g. dental restoratives and adhesives. These aromatic amines exhibit excellent color stability when the composition is cured, thereby eliminating or reducing the need for a UV stabilizer to be included in the formulation. A reduction in the amount of UV stabilizer in the composition results in an increased expression of fluorescence, which allows the composition to more closely mimic natural tooth fluorescence. The initiator systems of the invention are, therefore, particularly useful in curable resin/filler composite materials used in restorative dentistry where the long term aesthetic quality of the material is often important. Such compositions typically include, in addition to the initiator system, a polymerizable component, one or more fillers, and/or other additives depending on the desire application.

Polymerizable Component

The dental compositions of the present invention are hardenable, typically due to the presence of a polymerizable component. In some embodiments, the composition can be hardened (e.g., polymerized by conventional photopolymerization and/or chemical polymerization techniques) prior to applying it to an oral surface. In other embodiments, the composition can be hardened (e.g., polymerized by conventional photopolymerization and/or chemical polymerization techniques) after it has been applied to an oral surface.

In certain embodiments, the compositions are photopolymerizable, i.e., the compositions contain a photoinitiator system that upon irradiation with actinic radiation initiates the polymerization (or hardening) of the composition.

Such photopolymerizable compositions can be free radically polymerizable or cationically polymerizable. In other embodiments, the compositions are chemically hardenable, i.e., the compositions contain a chemical initiator (i.e., initiator system) that can polymerize, cure, or otherwise harden the composition without dependence on irradiation with actinic radiation. Such chemically hardenable compositions are sometimes referred to as "self-cure" compositions.

The polymerizable component typically includes one or more ethylenically unsaturated compounds with or without acid functionality. Examples of useful ethylenically unsaturated compounds include acrylic acid esters, methacrylic acid esters, hydroxy-functional acrylic acid esters, hydroxy-functional methacrylic acid esters, and combinations thereof.

The compositions, especially in photopolymerizable implementations, may include compounds having free radically active functional groups that may include monomers, oligomers, and polymers having one or more ethylenically unsaturated groups. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth) acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The polymerizable component may also contain hydroxyl groups and ethylenically unsaturated groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

In certain embodiments, the polymerizable component includes PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and/or NPGDMA (neopentylglycol dimethacrylate). Various combinations of these hardenable components can be used if desired.

When the composition contains an ethylenically unsaturated compound without acid functionality, it is generally present in an amount of at least 5% by weight, more typically at least 10% by weight, and most typically at least 15% by weight ethylenically unsaturated compounds without acid functionality, based on the total weight of the unfilled composition. The compositions of the present invention typically include at most 95% by weight, more typically at most 90% by weight, and most typically at most 80% by weight ethylenically unsaturated compounds without acid functionality, based on the total weight of the unfilled composition.

In some embodiments, the polymerizable component may include one or more ethylenically unsaturated compounds with acid functionality. As used herein, ethylenically unsaturated compounds "with acid functionality" is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl (meth) acrylate (e.g., HEMA)phosphates, bis((meth)acryloxyethyl) phosphate, ((meth)acryloxypropyl)phosphate, bis((meth) acryloxypropyl)phosphate, bis((meth)acryloxy)propyloxy phosphate, (meth)acryloxyhexyl phosphate, bis((meth)acryloxyhexyl)phosphate, (meth)acryloxyoctyl phosphate, bis ((meth)acryloxyoctyl)phosphate, (meth)acryloxydecyl phosphate, bis((meth)acryloxydecyl)phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly (meth)acrylated polysulfonate, poly(meth)acrylated polyboric acid, and the like, and may be used as components in the hardenable component system. Also monomers, oligomers, and polymers of unsaturated carbonic acids such as (meth) acrylic acids, aromatic (meth)acrylated acids (e.g., methacrylated trimellitic acids), and anhydrides thereof can be used. Certain preferred compositions of the present invention include an ethylenically unsaturated compound with acid functionality having at least one P—OH moiety.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in International Publication No. WO 2004/060327 (Abuelyaman et al.); AA:ITA: IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

Compositions of the present invention can also include combinations of ethylenically unsaturated compounds with acid functionality as described, for example, in International Publication No. WO 2006/020760 (Luchterhandt et al.). The compositions may also include a mixture of ethylenically unsaturated compounds both with and without acid functionality.

When the composition contains an ethylenically unsaturated compound with acid functionality, it is generally present in an amount of at least 1% by weight, more typically at least 3% by weight, and most typically at least 5% by weight ethylenically unsaturated compounds with acid functionality, based on the total weight of the unfilled composition. The compositions of the present invention typically include at most 80% by weight, more typically at most 70% by weight, and most typically at most 60% by weight ethylenically unsaturated compounds with acid functionality, based on the total weight of the unfilled composition.

Initiator System

In typical implementations of the invention, a free-radically polymerizable component is combined with a photoinitiator to provide a photopolymerizable composition. Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer (also referred to herein as a visible light sensitizer or visible light absorber), and an electron donor compound.

The photoinitiator system of the invention includes a color-stable amine electron donor that has at least one aromatic group and a hydrocarbyl group with an alpha hydrogen. The amine also typically has at least one hydrocarbyl group with an electron withdrawing group beta to the amine and a hydrogen on the same carbon atom beta to the amine.

The amine electron donors of the invention may be of the type shown below as formula I:

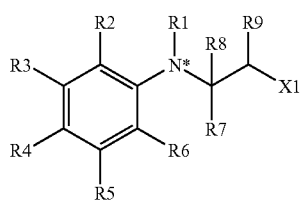

Formula I wherein

N* is a nitrogen atom;

R1 is an alkyl group having 1 to 16 carbon atoms, or is CH₂CH₂X2;

R2, R3, R4, R5, R6, R7, R8, and R9 are independently selected from hydrogen (H) or an alkyl group having 1 to 4 carbon (C) atoms, with the proviso that there is at least one hydrogen atom bonded to at least one of the carbon atoms that are bonded (i.e., at the alpha position) to the nitrogen atom N*;

X1 is selected from CO₂R10, C(O)R11, C(O)R10, and CONR10R11 and X2 is selected from CN, CO₂R10, C(O)R11, and C(O)R10, where each R10 and R11 are independently selected from H, alkyl groups having 1 to 6 carbon atoms, aryl groups, and aralkyl groups.

In some embodiments, the amine electron donors of the invention may be of type show below as Formula II:

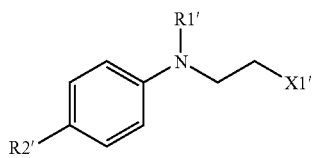

Formula II in which R1' is CH₃, CH₂-lower alkyl, or CH₂CH₂X2'; R2' is H, CH₃, or CH₂-lower alkyl; X1' and X2' are each independently selected from CN, CO₂R3', CHO, COR3', and CONR3'R4', where R3' and R4' are each independently selected from H, alkyl groups having 1 to 6 carbon atoms, aryl groups, and aralkyl groups. When R1' and/or R2' of Formula II are CH₂-alkyl, the alkyl component is typically a lower alkyl, i.e. a C₁ to C₄ alkyl (e.g., methyl, ethyl, propyl, butyl, etc.)

Suitable electron donors falling within Formula I and Formula II above include, but are not limited to, the following compounds:

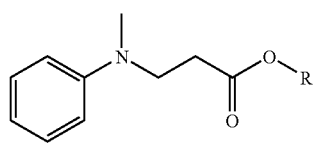

formula 1-a

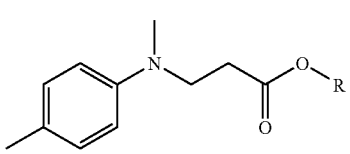

formula 1-b wherein R is an alkyl group having 1 to 4 carbon atoms.

The above compounds may be synthesized using known methods, such as those described by Adamson, et al.; JCSOA9; J. Chem. Soc.; 1949; spl. 144,152, which is incorporated herein by reference.

As described above, the initiator system of the invention contains a visible light absorber (i.e. photosensitizer) and may also optionally contain an iodonium salt, and/or one or more additional electron donors, such as a polycyclic aromatic compound, etc. The iodonium salt should be soluble in the composition and preferably is shelf-stable, meaning it does not spontaneously promote polymerization when dissolved therein in the presence of the visible light sensitizer and the electron donor compound. Accordingly, selection of a particular iodonium salt may depend to some extent upon the particular resin, visible light sensitizer and electron donor that are chosen. Suitable iodonium salts include, but are not limited to, the diaryl iodonium salts, e.g., diphenyliodonium chloride, diphenyliodonium hexafluorophosphate, diphenyliodonium tetrafluoroborate, tolylcumyliodonium tetrakis (pentafluorophenyl)borate, and the like.

The visible light sensitizer should be partly or fully soluble in the photopolymerizable composition, free of functionalities that would substantially interfere with the polymerization process, and capable of light absorption somewhere within the range of wavelengths between about 400 and about 1000 nanometers. Typical visible light sensitizers contain one or more carbonyl functional groups. Suitable photosensitizers include monoketones and diketones that absorb some light within a range of 400 nm to 520 nm (preferably, 450 nm to 500 nm) Particularly suitable compounds include alpha diketones that have light absorption within a range of 400 nm to 520 nm (even more preferably, 450 to 500 nm) Exemplary photosensitizer compounds include, but are not limited to, camphorquinone, benzil, furil, 3,3,6,6-tetramethylcyclohexanedione, phenanthraquinone, 1-phenyl-1,2-propanedione and other 1-aryl-2-alkyl-1,2-ethanediones, cyclic alpha diketones, and the like.

As described above, the photoinitiator system may also contain additional electron donors. Suitable additional electron donors include, but are not limited to, polycyclic aromatic compounds, e.g., biphenylenes, naphthalenes, anthracenes, benzanthracenes, pyrenes, azulenes, pentacenes, decacyclenes, and derivatives (such as acenaphthenes) and combinations thereof.

The individual components of the photoinitiator system are provided in photopolymerizingly effective amounts (i.e., amounts effective to yield a photoinitiator system that can initiate photopolymerization of the polymerizable component or, more preferably, that can accelerate the rate of polymerization). Typically, the visible light sensitizer is present at about 0.05-5.0 weight percent based on the overall photopolymerizable unfilled composition, more typically, at about 0.10-2.0 weight percent. The iodonium salt is typically present at about 0.05-10.0 weight percent, more typically at about 0.20-5.0 weight percent, and most typically at about 0.40-3.0 weight percent, based on the overall unfilled composition. The color-stable amine electron donor and/or additional electron donor(s) is typically present at about 0.01-5.0 weight percent, more typically about 0.05-1.0 weight percent, and most typically about 0.05-0.50 weight percent, based on the overall unfilled composition.

Although the compositions of the invention are typically photopolymerizable, in certain embodiments, the compositions of the present invention are chemically hardenable, i.e., the compositions contain a chemically hardenable component and a chemical initiator (i.e., initiator system) that can polymerize, cure, or otherwise harden the composition without dependence on irradiation with actinic radiation. In some embodiments of the invention, a combination of light-cure and self-cure systems may be used.

The chemically hardenable compositions may include redox cure systems that include a polymerizable component (e.g., an ethylenically unsaturated polymerizable component) and redox agents that include an oxidizing agent and a reducing agent. Suitable polymerizable components, redox agents, optional acid-functional components, and optional fillers that are useful in the present invention are described in U.S. Pat. Publication Nos. 2003/0166740 (Mitra et al.) and 2003/0195273 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Patent Publication No. 2003/0195273 (Mitra et al.).

The reducing and oxidizing agents are present in amounts sufficient to permit an adequate free-radical reaction rate. This can be evaluated by combining all of the ingredients of the composition except for the optional filler, and observing whether or not a hardened mass is obtained.

Typically, the reducing agent, if used at all, is present in an amount of at least 0.01% by weight, and more typically at least 0.1% by weight, based on the total weight (including water) of the components of the composition. Typically, the reducing agent is present in an amount of no greater than 10% by weight, and more typically no greater than 5% by weight, based on the total weight (including water) of the components of the composition.

Typically, the oxidizing agent, if used at all, is present in an amount of at least 0.01% by weight, and more typically at least 0.10% by weight, based on the total weight (including water) of the components of the composition. Typically, the oxidizing agent is present in an amount of no greater than 10% by weight, and more typically no greater than 5% by weight, based on the total weight (including water) of the components of the composition.

The reducing or oxidizing agents can be microencapsulated as described in U.S. Pat. No. 5,154,762 (Mitra et al.). This will generally enhance shelf stability of the composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, including photoinitiator systems or with a composition such as described U.S. Pat. No. 5,154,762 (Mitra et al.).

Filler(s)

The compositions of the present invention may optionally contain one or more fillers. Fillers may be selected from one or more of a wide variety of materials suitable for incorporation in compositions used for dental applications, such as fillers currently used in dental restorative compositions, and the like.

The choice of the filler affects important properties of the dental composite such as its appearance, radiopacity and physical and mechanical properties. Appearance is affected in part by adjustment of the amounts and relative refractive indices of the ingredients of the composite, thereby allowing alteration of the translucence, opacity or pearlescence of the composite. In this way, the appearance of the dental material can, if desired, be made to closely approximate the appearance of natural dentition.

Radiopacity is a measurement of the ability of the dental composite to be detected by x-ray examination. Frequently a radiopaque dental composite will be desirable, for instance, to enable the dentist to determine whether or not a dental restoration remains sound. Under other circumstances a non-radiopaque composite may be desirable. Suitable fillers for radiopaque formulations are described in EP-A2-0 189 540, EP-B-0 238 025, and U.S. Pat. No. 6,306,926 B1.

The amount of filler that is incorporated into the composite, referred to herein as the "loading level" and expressed as a weight percent based on the total weight of the dental material, will vary depending on the type of filler, the curable resin and other components of the composition, and the end use of the composite.

For some dental materials, such as sealants, the compositions of the invention can be lightly filled (e.g., having a loading level of less than about 40 weight percent) or unfilled. In such implementations, the viscosity of the dental material is sufficiently low to allow its penetration into pits and fissures of occlusal tooth surfaces as well as into etched areas of enamel, thereby aiding in the retention of the dental material. In applications where high strength or durability are desired (e.g., anterior or posterior restoratives, prostheses, crown and bridge cements, artificial crowns, artificial teeth and dentures) the loading level can be as high as about 95 weight percent. For most dental restorative and prosthetic applications a loading level is generally at least 40 weight percent, and more typically is between about 60 and 90 weight percent.

The filler(s) used in the compositions of the invention is typically finely divided. The filler(s) can have a unimodal or polymodal (e.g., bimodal) particle size distribution. The maximum particle size (the largest dimension of a particle, generally, the diameter) of the filler(s) is typically less than 20 micrometers, more typically less than 10 micrometers, and most typically less than 5 micrometers. The average particle size of the filler(s) is typically less than 0.1 micrometers, and more typically less than 0.075 micrometer.

The filler(s) may be an inorganic material. It may also be a crosslinked organic material that is insoluble in the resin system, and is optionally filled with inorganic filler. The filler(s) should in any event be nontoxic and suitable for use in the mouth. The filler(s) can be radiopaque or radiolucent. The filler typically is substantially insoluble in water.

Examples of suitable inorganic fillers are naturally occurring or synthetic materials including, but not limited to: quartz (i.e. silica, $SiO_2$); nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers such as those described in U.S. Pat. No. 4,695, 251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). In some embodiments, the silica or nanosilica particles are non-pyrogenic, i.e. comprise non-fumed silica. Examples of suitable organic filler particles include filled or unfilled pulverized polycarbonates, polyepoxides, and the like.

The filler may be acid-reactive, non-acid-reactive, or a combination thereof Suitable non-acid-reactive filler particles include quartz, submicron silica, nano silica, nano zirconia, and non-vitreous microparticles of the type described in U.S. Pat. No. 4,503,169 (Randklev). Mixtures of these non-acid-reactive fillers are also contemplated, as well as combination fillers made from organic and inorganic materials. Silane-treated zirconia-silica (Zr—Si) filler is especially useful in certain embodiments. In some implementations of the invention, the filler system may contain a combination of at least one filler comprising heavy metal oxide nanoparticles (e.g., zirconia nanoparticles), and/or at least one filler comprising non-heavy metal oxide particles (e.g. silica nanoparticles), and/or at least one filler comprising a heavy metal oxide and a non-heavy metal oxide (e.g. clusters of zirconia and silica nanoparticles).

Metallic fillers may also be incorporated, such as particulate metal filler made from a pure metal such as those of Groups IVA, VA, VIA, VIIA, VIII, IB, or IIB, aluminum, indium, and thallium of Group IIIB, and tin and lead of Group IVB, or alloys thereof. Conventional dental amalgam alloy powders, typically mixtures of silver, tin, copper, and zinc, may also optionally be incorporated. The particulate metallic filler preferably has an average particle size of about 1 micron to about 100 microns, more preferably 1 micron to about 50 microns. Mixtures of these fillers are also contemplated, as well as combination fillers made from organic and inorganic materials. Fluoroaluminosilicate glass fillers, either untreated or silanol treated, are particularly preferred. These glass fillers have the added benefit of releasing fluoride at the site of dental work when placed in the oral environment.

In some implementations, the composition may include acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass, if present, typically contains sufficient elutable cations so that a hardened dental composition will form when the glass is mixed with the components of the hardenable composition. The glass also typically contains sufficient elutable fluoride ions so that the hardened composition will have cariostatic properties. Such glass can be made from a melt containing fluoride, alumina, and other glass-forming ingredients using techniques familiar to those skilled in the FAS glassmaking art. The FAS glass, if present, is typically in the form of particles that are sufficiently finely divided so that they can conveniently be mixed with the other cement components and will perform well when the resulting mixture is used in the mouth.

Generally, the average particle size (typically, diameter) for FAS glass used in such compositions is no greater than about 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEM-FIL Superior (Dentsply International, York, Pa.). Mixtures of fillers can be used if desired.

The surface of the filler particles can also be treated with a coupling agent in order to enhance the bond between the filler and the resin. Suitable coupling agents include gamma-methacryloxypropyltrimethoxysilane, gamma-mercaptopropyltriethoxysilane, gamma-aminopropyltrimethoxysilane, and the like. Silane-treated zirconia-silica ($ZrO_2$-$SiO_2$) fillers and nanofillers, silane-treated silica fillers and nanofillers, silane-treated zirconia fillers and nanofillers, and combinations thereof are especially suitable for certain restorative compositions.

Other suitable fillers are disclosed in U.S. Pat. No. 6,387, 981 (Zhang et al.); U.S. Pat. No. 6,572,693 (Wu et al.); U.S. Pat. No. 6,730,156 (Windisch); and U.S. Pat. No. 6,899,948 (Zhang); as well as in International Publication No. WO 03/063804 (Wu et al.). Filler components described in these references include nanosized silica particles, nanosized metal oxide particles, and combinations thereof. Nanofillers are also described in U.S. Patent Publication Nos. 2005/0252413 (Kangas et al.); 2005/0252414 (Craig et al.); and 2005/0256223 (Kolb et al.).

For some embodiments of the present invention that include filler (e.g., dental adhesive compositions), the compositions typically include at least 1% by weight, more typically at least 2% by weight, and most typically at least 5% by weight filler, based on the total weight of the composition. For such embodiments, compositions of the present invention typically include at most 40% by weight, more typically at most 20% by weight, and most typically at most 15% by weight filler, based on the total weight of the composition.

For other embodiments (e.g., wherein the composition is a dental restorative or an orthodontic adhesive), compositions of the present invention typically include at least 40% by weight, more typically at least 45% by weight, and most typically at least 50% by weight filler, based on the total weight of the composition. For such embodiments, compositions of the present invention typically include at most 90% by weight, more typically at most 80% by weight, even more typically at most 70% by weight filler, and most typically at most 50% by weight filler, based on the total weight of the composition.

Other Additvies

Optionally, compositions of the present invention may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), or mixtures thereof.

In some implementations of the invention, the compositions are non-aqueous. In other implementation, the compositions may optionally contain water. The water can be distilled, deionized, or plain tap water. If present, the amount of water should be sufficient to provide adequate handling and mixing properties and/or to permit the transport of ions, particularly in a filler-acid reaction. In such embodiments, water represents at least about 1 wt-%, and more preferably at least about 5 wt-%, of the total weight of ingredients used to form the hardenable composition. Generally, water represents no greater than about 75 wt-%, and more preferably no greater than about 50 wt-%, of the total weight of ingredients used to form the hardenable composition.

If desired, the compositions of the invention may contain additives such as indicators, dyes (including photobleachable dyes), pigments, inhibitors, accelerators, viscosity modifiers, wetting agents, antioxidants, tartaric acid, chelating agents, buffering agents, stabilizers, diluents, and other similar ingredients that will be apparent to those skilled in the art. Surfactants, for example, nonionic surfactants, cationic surfactants, anionic surfactants, and combinations thereof, may optionally be used in the compositions. Useful surfactants include non-polymerizable and polymerizable surfactants. Additionally, medicaments or other therapeutic substances can be optionally added to the dental compositions. Examples include, but are not limited to, fluoride sources, whitening agents, anticaries agents (e.g., xylitol), remineralizing agents (e.g., calcium phosphate compounds and other calcium sources and phosphate sources), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions. Combinations of any of the above additives may also be employed.

The selection and amount of any one such additive can be selected by one of skill in the art to accomplish the desired result without undue experimentation.

Preparation and Use of the Compositions

The dental compositions of the present invention can be prepared by combining all the various components using conventional mixing techniques. The resulting composition may optionally contain fillers, solvents, water, and other additives as described herein. Typically, photopolymerizable compositions of the invention are prepared by simply admixing, under "safe light" conditions, the components of the inventive compositions. Suitable inert solvents may be employed if desired when effecting this mixture. Any solvent may be used which does not react appreciably with the components of the inventive compositions. Examples of suitable solvents include acetone, dichloromethane, acetonitrile and lactones. A liquid material to be polymerized may be used as a solvent for another liquid or solid material to be polymerized. Solventless compositions can be prepared by simply dissolving the iodonium complex salt, sensitizer, and electron donor in the polymerizable resin, with or without the use of mild heating to facilitate dissolution.

The amounts and types of each ingredient in the dental material should be adjusted to provide the desired physical and handling properties before and after polymerization. For example, the polymerization rate, polymerization stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on previous experience with dental materials. When the dental material is applied to a tooth, the tooth can optionally be pre-treated with a primer and/or an adhesive by methods known to those skilled in the art.

The compositions can be supplied in a variety of forms including one-part systems and multi-part systems, e.g., two-part powder/liquid, paste/liquid, paste/powder and paste/paste systems. Other forms employing multi-part combinations (i.e., combinations of two or more parts), each of which is in the form of a powder, liquid, gel, or paste are also possible. The various components of the composition may be divided up into separate parts in whatever manner is desired; however, in a redox multi-part system, one part typically contains the oxidizing agent and another part typically contains the reducing agent, though it is possible to combine the reducing agent and oxidizing agent in the same part of the system if the components are kept separated, for example, through use of microencapsulation. Also, for those implementations in which the dental composition is a resin-modified glass ionomer (RMGI), the polyacid, acid-reactive filler and water generally would not all be present in the same part, although any two of these may be grouped together in the same part along with any combination of other components.

The components of the composition can be included in a kit, where the contents of the composition are packaged to allow for storage of the components until they are needed.

The components of the composition can be mixed and clinically applied using conventional techniques. A curing light is generally required for the initiation of photopolymerizable compositions. The compositions may be in the form of composites or restoratives that adhere very well to dentin and/or enamel. Optionally, a primer layer can be used on the tooth tissue on which the hardenable composition is used.

The invention encompasses a wide variety of dental compositions, which may be filled or unfilled. Exemplary dental materials include dental restoratives (e.g., composites, fillings, sealants, inlays, onlays, crowns, and bridges), orthodontic appliances, and orthodontic adhesives. Such dental materials include direct aesthetic restorative materials (e.g., anterior and posterior restoratives), prostheses, adhesives and primers for oral hard tissues, sealants, veneers, cavity liners, orthodontic bracket adhesives for use with any type of bracket (such as metal, plastic and ceramic), crown and bridge cements, artificial crowns, artificial teeth, dentures, and the like. These dental materials are used in the mouth and are disposed adjacent to natural teeth. The phrase "disposed adjacent to" as used herein refers to the placing of a dental material in temporary or permanent bonding (e.g., adhesive) or touching (e.g., occlusal or proximal) contact with a natural tooth.

The features and advantages of this invention are further illustrated by the following examples, which are in no way intended to be limiting thereof. The particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

Unless otherwise noted, all reagents and solvents were or can be obtained from Sigma Aldrich Corp., St. Louis, Mo.

As used herein,
"bisGMA" refers to 2,2-bis[4-(2-hydroxy-3-methacryloyloxypropoxy)phenyl]propane;
"TEGDMA" refers to triethyleneglycol dimethacrylate, obtained from Sartomer Co., Inc., Exton, Pa.;
"UDMA" refers to diurethane dimethacrylate, obtained under the trade designation "ROHAMERE 6661-0" from Rohm America LLC, Piscataway, N.J.;
"BisEMA" refers to ethoxylated bisphenol A dimethacrylate, obtained from Sartomer Co., Inc., Exton, Pa.;
"BHT" refers to butylated hydroxytoluene;
"Zr—Si FILLER" refers to silane-treated zirconia-silica filler prepared as described in U.S. Pat. No. 4,503,169 (Randklev);
"CPQ" refers to camphorquinone;
"EDMAB" refers to ethyl 4-dimethylaminobenzoate;
"DPIPF6" refers to diphenyliodonium hexafluorophosphate, obtained from Alfa Aesar, Ward Hill, Mass.;
"TINUVIN" refers to a polymerizable UV stabilizer obtained under the trade designation TINUVIN R 796 from Ciba Specialty Chemicals, Tarrytown, N.Y.;
"Zr—Si FILLER" refers to silane-treated zirconia-silica nanocluster filler prepared essentially as described in U.S. Pat. No. 6,730,156;
"SILICA FILLER" refers to a silane-treated nano-sized silica having a nominal particle size of approximately 20 nanometers, prepared essentially as described for FILLER F in U.S. Patent Publication No. 2005/0252413;
"LUMILUX" refers to a luminescent pigment available from Honeywell International Specialty Materials, Morristown, N.J.;
"ENMP" refers to ethyl N-methyl-N-phenyl-3-aminopropionate, a compound of Formula 1-a;
"NMPN" refers to N-methyl-N-phenyl-3-aminopropionitrile, a compound of Formula II;

Color Test Method

Initial and final colors were determined using a HunterLab Ultrascan XE Spectrocolorimeter (Reston, Va.). The spectrocolorimeter was standardized using a Diffuse/8° light trap followed by a Diffuse/8° instrument standard (U3322) (L*: 98.99; a*: −0.29; b*: −0.21). The instrument standard was calibrated by direct comparison to HunterLab Master Transfer Standards which are traceable to NIST (National Institute of Standards and Technology). In this method, a small area view was used with a port size of 25.4 millimeters (1 inch) in diameter. Cured samples were obtained as described below for each Example. Color data (L*a*b*) were measured immediately after each sample was cured. The sample was then aged by submersion in water at 37° C. for 24 hours while it was illuminated with a xenon lamp. Color data were then measured on the sample. Delta E was calculated as the total color change in the three color dimensions and is described by the following equation: Delta E=Square root $[(L_1*-L_2*)^2+(a_1*-a_2*)^2+(b_1*-b_2*)^2]$ where subscripts "1" indicate initial cured state and "2" indicate final aged state.

Determination of Diametral Tensile Strength (DTS) and Compressive Strength (CS)

Diametral tensile strength and compressive strength were determined according to ANSI/ADA specification No. 27 (1993). Each composition was injected into a glass tube having an inside diameter of 4 millimeters, and then the packed tube was then capped with silicone rubber plugs. The composition was then compressed axially at approximately 0.28 MPa (approximately 40.62 pounds per square inch) for 5 minutes. While under compression, the sample was then light cured for 90 seconds by exposure to a Model XL 1500 dental curing light (manufactured by 3M ESPE Dental Products, St. Paul, Minn.) and was then irradiated for 90 seconds in a Model UNIXS light curing box (manufactured by Heraeus Kulzer, Hanau, Germany). The cured sample was then cut crosswise using a diamond saw to afford discs having a length of approximately 2 millimeters (for the DTS test) or approximately 8 millimeters (for the CS test). The discs were stored in distilled water at 37° C. for 24 hours prior to testing. The DTS and CS tests were carried out on a Model 4505 Instron tester (manufactured by Instron Corp., Norwood, Mass.) with a 10-kilonewton (kN) load cell and at a crosshead speed of 1 meter per minute. Five discs of each cured composition were prepared and tested for DTS. Six discs of each cured composition were prepared and tested for CS.

Examples 1-2 and Comparative Examples 1-2

The compositions of Examples 1-2 and Comparative Examples 1-2 were prepared by first combining the components in the proportions as identified in Table 1 to provide resin mixtures A-D. In Table 1, all percentages are weight percentages, and "n/a" means that the component was not included in the composition.

TABLE 1

Resin Systems of Examples 1-2 and Comparative Examples 1-2.

| Component | Resin A | Resin B | Resin C | Resin D |
|---|---|---|---|---|
| bisGMA | 24.30% | 24.30% | 24.30% | 24.343% |
| UDMA | 37.06% | 37.06% | 37.06% | 37.60% |
| bisEMA | 27.69% | 27.69% | 27.69% | 27.60% |
| TEGDMA | 8.69% | 8.69% | 8.69% | 8.35% |
| CPQ | 0.516% | 0.516% | 0.516% | 0.506% |
| DPIHFP | 0.59% | 0.59% | 0.59% | 0.58% |
| BHT | 0.343% | 0.343% | 0.343% | 0.337% |

TABLE 1-continued

Resin Systems of Examples 1-2 and Comparative Examples 1-2.

| Component | Resin A | Resin B | Resin C | Resin D |
|---|---|---|---|---|
| TINUVIN | 0.312% | 0.312% | 0.312% | 2.296% |
| EDMAB | n/a | n/a | 0.496% | 2.39% |
| ENMP | 0.496% | n/a | n/a | n/a |
| NMPN | n/a | 0.496% | n/a | n/a |

The compositions of Examples 1-2 and Comparative Examples 1-2 were prepared by combining a portion of each of Resins A-D (19.746 g each), respectively, with silica filler (6.671 g), Zr—Si filler (63.529 g), and LUMILUX (0.054 g) using a Model DAC 150 FVZ SpeedMixer (manufactured by FlackTek, Inc., Landrum, S.C.) at 3000 rpm. A disk of each composition having a thickness of one millimeter and a diameter of thirty millimeters was prepared and cured for two minutes in a hydraulic press (obtained from Carver, Inc., Wabash, Ind.) at 68.95 MPa (10,000 pounds per square inch) pressure. The press had been fitted with fiber optic cables to direct light to the disk from a Model A20500 ACE light source (Schott North America, Inc., Auburn, N.Y.). The disk was removed from the press and was further cured for 90 seconds using a stroboscopic light curing device (UNISX; Heaeus Kulzer, Inc., Armonk, N.Y.). The color of each cured disk was measured, before and after illumination during immersion in water at 37° C., as described above. The Delta E values for each of the compositions were found to be 6.2 (Example 1), 6.0 (Example 2), 8.4 (Comparative Example 1), and 9.1 (Comparative Example 2).

Example 3 and Comparative Examples 3-4

The compositions of Example 3 and Comparative Example 3 were prepared by first combining the components in the proportions as identified in Table 2 to provide resin mixtures E and F. The composition of Comparative Example 4 was a commercially available composite dental restorative (available under the trade designation FILTEK SUPREME UNIVERSAL RESTORATIVE from 3M ESPE Dental Products, St. Paul, Minn.). In Table 2, all percentages are weight percentages, and "n/a" means that the component was not included in the composition.

TABLE 2

Resin Systems of Example 3 and Comparative Example 3.

| Component | Resin E | Resin F |
|---|---|---|
| bisGMA | 24.28% | 23.34% |
| UDMA | 37.02% | 35.60% |
| bisEMA | 27.66% | 26.60% |
| TEGDMA | 8.68% | 8.35% |
| CPQ | 0.52% | 0.506% |
| DPIHFP | 0.59% | 0.581% |
| BHT | 0.34% | 0.337% |
| TINUVIN | 0.39% | 2.296% |
| EDMAB | n/a | 2.39% |
| ENMP | 0.52% | n/a |

The compositions of Example 3 and Comparative Example 3 were prepared by combining a portion of each of Resins E and F (2.588 g each), respectively, with silica filler (0.896 g), Zr—Si filler (8.525 g), and LUMILUX (0.0117 g) using a Model DAC 150 FVZ SpeedMixer (manufactured by Flack-Tek, Inc., Landrum, S.C.) at 3000 rpm. A disk of each of these compositions and of the composition of Comparative Example 4 was cured essentially as described above. The color of each cured disk was measured, before and after illumination during immersion in water at 37° C., as described above. The Delta E values for each of the compositions were found to be 4.31 (Example 3), 9.1 (Comparative Example 3), and 5.6 (Comparative Example 4). The diametral tensile strength (DTS) and compressive strength (CS) of each of the cured samples of Example 3 and Comparative Example 4 were determined as described above. The DTS values were found to be 69.63 MPa (Example 3) and 63.82 MPa (Comparative Example 4). The CS values were found to be 336.7 MPa (Example 3) and 335.2 MPa (Comparative Example 4).

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A hardenable dental composition comprising:

a polymerizable component; and an initiator system comprising at least one electron donor having the following formula:

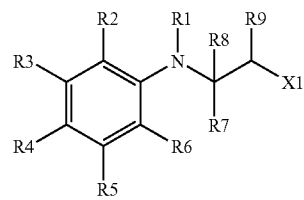

wherein

N is nitrogen;

R1 is an alkyl group having 1 to 16 carbon atoms, or is $CH_2CH_2X2$;

R2, R3, R4, R5, R6, R7, R8 and R9 are independently selected from H or an alkyl group having 1 to 4 carbon atoms, with the proviso that at least one carbon atom at a position alpha to the nitrogen is bonded to at least one hydrogen atom;

X1 is selected from $CO_2R10$, $C(O)R11$, $C(O)R10$, and $CONR10R11$ and X2 is selected from CN, $CO_2R10$, $C(O)R11$, and $C(O)R10$, where each R10 and R11 are independently selected from H, alkyl groups having 1 to 6 carbon atoms, aryl groups, and aralkyl groups.

2. The composition of claim 1, where in R1 is $CH_3$, $CH_2$-(lower alkyl), or $CH_2CH_2X2$;

R2 and R6 are independently H or $CH_3$;

R3 and R5 are H;

R4 is H, $CH_3$ or $CH_2$- (lower alkyl); and

R7, R8, R9 and R10 are H.

3. The composition of claim 1, wherein the electron donor has the following formula:

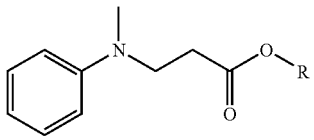

wherein R is an alkyl group having 1 to 4 carbon atoms.

4. The composition of claim 1, wherein the electron donor has the following formula:

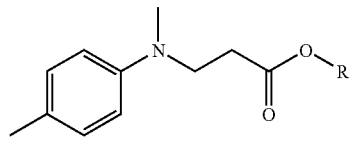

wherein R is an alkyl group having 1 to 4 carbon atoms.

5. The composition of claim 1, wherein the polymerizable component comprises an ethylenically unsaturated component.

6. The composition of claim 5, wherein the ethylenically unsaturated component comprises a meth(acrylate).

7. The composition of claim 1, wherein the initiator system further comprises a visible light absorber.

8. The composition of claim 7, wherein the visible light absorber comprises camphorquinone (CPQ).

9. The composition of claim 1, wherein the initiator system further comprises an iodonium salt.

10. The composition of claim 9, wherein the iodonium salt is diphenyliodonium hexafluorophosphate.

11. The composition of claim 1, wherein the initiator system further comprises an second electron donor.

12. The composition of claim 11, wherein the second electron donor comprises a polycyclic aromatic compound.

13. The composition of claim 12, wherein the polycyclic aromatic component is selected from the group consisting of an anthracene derivative, a biphenylene derivative, and combinations thereof.

14. The composition of claim 1, further comprising a filler.

15. The composition of claim 14, wherein the filler comprises nanoparticles.

16. The composition of claim 1, wherein the composition is substantially free of UV stabilizers.

17. The composition of claim 1, wherein the composition has natural tooth fluorescence.

18. A photoinitiator system comprising:
a visible light absorber;
an iodonium salt; and
at least one electron donor having the following formula:

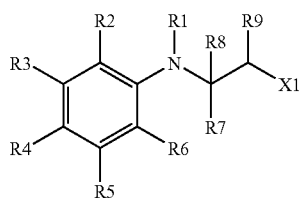

wherein
N is nitrogen;
R1 is an alkyl group having 1 to 16 carbon atoms, or is —CH$_2$—CH$_2$X2;
R2, R3, R4, R5, R6, R7, R8, and R9 are independently selected from H or an alkyl group having 1 to 4 carbon atoms, with the proviso that at least one carbon atom at a position alpha to the nitrogen is bonded to at least one hydrogen atom;
X1 is selected from CO$_2$R10, C(O)R11, C(O)R10, and CONR10R11 and X2 is selected from CN, CO$_2$R10, C(O)R11, and C(O)R10, where each R10 and R11 are independently selected from H, alkyl groups having 1 to 6 carbon atoms, aryl groups, and aralkyl groups.

19. The photoinitiator system of claim 18, wherein the electron donor has the following formula:

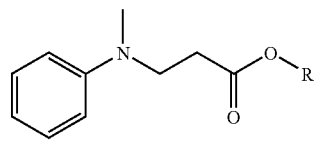

wherein R is an alkyl group having 1 to 4 carbon atoms.

20. The photoinitiator system of claim 18, wherein the electron donor has the following formula:

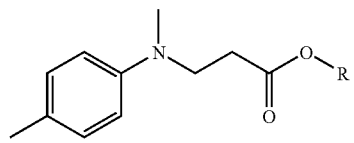

wherein R is an alkyl group having 1 to 4 carbon atoms.

21. The photoinitiator system of claim 18, wherein the visible light absorber comprises camphorquinone (CPQ).

22. The photoinitiator system of claim 18, wherein the iodonium salt comprises diphenyliodonium hexafluorophosphate.

23. The photoinitiator system of claim 18, wherein the photoinitiator system further comprises a second electron donor.

24. The photoinitiator system of claim 23, wherein the second electron donor comprises a polycyclic aromatic compound.

25. The photoinitiator system of claim 24, wherein the polycyclic aromatic component is selected from the group consisting of an anthracene derivative, a biphenylene derivative, and combinations thereof.

26. A hardenable composition comprising a polymerizable component and a photoinitiator system of claim 18.

27. A dental article made by polymerizing the composition of claim 1.

* * * * *